US005897863A

United States Patent [19]
Robson et al.

[11] Patent Number: 5,897,863
[45] Date of Patent: Apr. 27, 1999

[54] LHRH HORMONES

[75] Inventors: Barry Robson, Stockport; Robert V. Fishleigh, Manchester, both of United Kingdom

[73] Assignee: Proteus Molecular Design Limited, United Kingdom

[21] Appl. No.: 08/484,839

[22] Filed: Jun. 7, 1995

Related U.S. Application Data

[62] Division of application No. 07/908,659, Jul. 2, 1992, Pat. No. 5,780,035, which is a continuation of application No. 07/177,730, Apr. 5, 1988, abandoned.

[30] Foreign Application Priority Data

Jun. 5, 1987 [GB] United Kingdom .................. 8713240
Oct. 1, 1987 [GB] United Kingdom .................. 8723072

[51] Int. Cl.$^6$ ......................... A61K 38/09; A61K 38/24; A61K 39/385; C07K 14/00
[52] U.S. Cl. .................................. 424/185.1; 424/192.1; 424/195.11; 424/198.1; 514/12; 514/13; 514/14; 530/313; 530/324; 530/325; 530/326
[58] Field of Search .................................... 530/313, 326, 530/329, 324; 424/198.1, 192.1, 195.11, 185.1, 184.1; 514/14, 151, 6

[56] References Cited

U.S. PATENT DOCUMENTS

| | | | |
|---|---|---|---|
| 3,963,691 | 6/1976 | Hoffman et al. ........................ | 530/313 |
| 4,460,503 | 7/1984 | Suarda et al. ............................ | 530/328 |
| 4,608,251 | 8/1986 | Mia ........................................ | 530/313 |
| 4,639,512 | 1/1987 | Audibert et al. ........................ | 530/313 |
| 4,713,366 | 12/1987 | Stevens ................................... | 514/313 |
| 4,935,419 | 6/1990 | Tolkers et al. .......................... | 530/313 |
| 4,975,420 | 12/1990 | Silversides .............................. | 530/313 |
| 5,110,904 | 5/1992 | Haviv et al. ............................. | 53/313 |

FOREIGN PATENT DOCUMENTS

| | | | |
|---|---|---|---|
| 0142387 | 5/1985 | European Pat. Off. ............... | 530/328 |
| 9011298 | 10/1990 | WIPO . | |

OTHER PUBLICATIONS

Morrison et al. "Computerpaided design and physiological testing of a lutening hormone–releasing . . . ", *Fed. of Eur Biochem Soc*, 214(1):65–70, 1987.
Arshady et al. "Peptide Synthesis. Part 1. Preparation and Use of Polar Supports . . . ", *J Chem Soc Perkin Trans*, 1:529–537, 1981.
Atherton et al. "Peptide Synthesis. Part 3. Comparative Solid–phase Syntheses of Human . . . ", *J Chem Soc Perkin Trans*, 3:65–73, 1983.
Lachmann et al. "Raising antibodies by copling peptides to PPD . . . ", *Ciba Foundation Symposium 119*, pp. 25–43, 1986.
Carelli et al. "Immunological castration of male mice by a totally synthetic vaccine . . . ", *Proc Natl Acad Aci USA*, 79:5392–5395, 1982.
Carelli et al. "Immunological castration by a totally synthetic vaccine . . . ", *Int J Immunopharmac*, 7(2):215–224, 1985.
Lee et al. *Molecular Immunology*, 17:749–756, 1980.
*The Merck Manual*, 11th ed. pp. 640–643 (1966).
Eidine et al. "Gonadotropin–Releasing Hormone Bindin Sites in Human Breast Carcinoma", *Science*, 229:989–991, 1985.
Manni et al. "Treatment of Breast Cancer with Gonadotrpoin–Releasing Hormone", *Endocrine Reviews*, 7(1):89–94, 1986.
Robertson et al. "Effect of immunological castration on sexual and production . . . " *The Veterinary Record*, pp. 529–531, 1982.
Furr et al. "Use of Analogues of Lutenizing Hormone–Releasing Hormone for the Treatment of Cancer", *J Reprod Fert*, 64:529–539, 1982.
Redding et al. "Inhibition of Prostate Tumor Growth in Two Rat Models by Chronic Administration of . . . ", *Medical Sciences*, 78(10):6509–6512, 1981.
Newrath et al. Europ. Patent Appln., 14pp (1981), *Chem Abs.* 12(23), 215074.
Ramadandran et al. PCT Int'l Appln., 61 pp. (1980) *Chem Abs*, 113(11), 94359a.
Silversides *J Reprod Immun*, 13(3):249–261, 1988, *Chem Abs*, 109(25), 222687.
Coy et al. *Endocrinology*, 110(4):1445–1447, 1982.
Dutta *Drugs of the Future*, 13(8):761–787, 1988.
Spriggs et al. "Experiments Using the LHRH–GC Analogue Coupled To a Variety of Polypeptide Carriers", *Topics in Vaccine Research*, pp. 109–118, 1990.
Gonzales et al. *J Reprod Fert Suppl*, 39:189–198, 1989.
Ljungquist et al. *Biochemical & Biophysical Research Comunication*, 148(2):849–856, 1987.
Seeburg et al (1984) Nature 311:666–668.
Adelman et al(1986) Proc. Natl. Acad. Sci USA 83:179–183.
*Laboratory Technologies in Biochemistry and Molecular Biology* vol. 19 ed by Budon and Knippenberg Chapter 1 pp. 1–39, 1988 Elsevier Amsterdam.
S. Davis Scrip Magazine May 1992 pp. 34–38.
Fishleigh (Sep. 1992) "Development of New Methods for the Podiction of Polypeptide Conformation" Abstr.
Lee (Oct. 1992) Pharmaceutical Technology International pp. 59–64.
*Introduction to Proteins and Protein Engineering* Robson and Garnier (1988) Elsevier, Amsterdam pp. 597–637.

*Primary Examiner*—Ponnathapura Achutamurthy
*Attorney, Agent, or Firm*—Foley & Lardner

[57] ABSTRACT

An analogue of lutenising hormone-releasing hormone (LHRH) having the amino acid sequence: pGlg-His-Trp-Ser-Tyr-X-Len-Arg-Pro-Gly-Y-Z wherein X represents Gly or a D-amino acid, Y represents one or more amino acid residues, which may be the same or different, and Z represents Cys or Tyr, such that the solution conformation of said analogue is substantially similar to that of native LHRH. The analogues may be used to prepare vaccines for reducing fertility in mammals.

13 Claims, 3 Drawing Sheets

Steroscopic diagrams of the predicted lowest energy solution conformers of (a) mammalian LHRH, and (b) the LHRH-Gly-Cys-OH analogue.

a b

Day 70 anti-LHRH-Gly-Cys-OH antibody titres in rats immunised with various LHRH-Gly-Cys-OH conjugates.

Effect of immunisation with various LHRH-Gly-Cys-OH conjugates on testicular weight in rats.

LHRH HORMONES

This application is a divisional of application Ser. No. 07/908,659, filed Jul. 2, 1992, now U.S. Pat. No. 5,780,035, which is a continuation of Ser. No. 07/177,730, filed Apr. 5, 1998 abandoned.

BACKGROUND OF THE INVENTION

The present invention relates to extended analogues of the mammalian hormone referred to as luteinising hormone-releasing hormone (LHRH). In particular, it relates to analogues of LHRH formed by adding to the C-terminus of the native LHRH amino acid sequence a short additional amino acid sequence ending with a cysteine residue, such that the conformation in solution is substantially unchanged, and polypeptide conjugates thereof suitable for raising anti-LHRH antibodies.

LHRH is a decapeptide having the amino acid sequence
pGlg-His-Trp-Ser-Tyr-Gly-Leu-Arg-Pro-GlyNH$_2$ wherein pglg represents a pyroglutamate residue and GlyNH$_2$ represents glycine-amide, In mammals, this hormone is secreted by the hypothalamus and is responsible for controlling the release of luteinising hormone and follicle-stimulating hormone from the pituitary (Schally et al., Science (1973) 179, 341–350; Guillemin, R., Contraception (1972) 5, 1–32). The latter hormones are directly involved in controlling the development and the normal physiological functioning of testes and ovaries.

Active immunisation of various mammals to LHRH, eg. rats, rabbits, sheep and cattle, has been shown to lead in the case of males to testicular regression, reduction of testosterone secretion and cessation of spermatogensis and in the case of females to loss of cycling and ovarian regression, and it has long been appreciated that active immunisation to LHRH could provide a desirable means for routinely reducing fertility in domestic mammals and farm animals, particularly bull calves. In a comparative study of steer calves and immunologically-castrated calves produced by active immunisation to LHRH, the so-called "immunocastrates" were found to be superior in terms of their carcase composition since in these animals anabolic influence of the testes was not totally abolished (Robertson et al., Veterinary Record (1982) 111, 529–531). Moreover, surgical castration involves a degree of risk of infection and trauma, particularly if attempted on other than very young animals. Nevertheless, active immunisation to LHRH using a polypeptide conjugate of LHRH has previously required deleterious adjuvants and moreover the polypeptide conjugates themselves have been immunogenically unsatisfactory.

Hitherto published procedures for the conjugation of LHRH to a polypeptide carrier, e.g. bovine or human serum albumin, tetanus toxoid or thyroglobulin, have generally involved condensation of the hormone with a water-soluble carbodiimide. The absence of free carboxyl or amino moieties in LHRH means that coupling in such methods is probably effected through the hydroxyl group of Ser$^4$ or via a carboxy-methylated derivative of His$^2$. As a result, the immunogen is poorly-defined and unlikely to retain all the structural features of free LHRH in solution as considered desirable from the point of view of obtaining anti-LHRH antibodies capable of blocking functioning of LHRH in vivo; there is a danger that the peptide is attached through a region important for immunological recognition. Effective immunisation of mammals using such conjugates to provide a high titre of anti-LHRH antibodies capable of significantly reducing the biological efficacy of endogenous LHRH has only been achieved in the presence of an adjuvant liable to cause undesirable side effects, most commonly Freund's complete or incomplete adjuvant. Freund's complete adjuvant interferes with the tuberculin test in cattle and in addition this adjuvant and also Freund's incomplete adjuvant cause a variable amount of chronic inflammatory reaction at the site of injection. Such procedures have accordingly achieved no practical importance.

A totally synthetic LHRH vaccine based on muramyl dipeptide (MDP) has recently been shown to be capable of effecting immunological castration in male mice (Carelli et al., Proc. Nat. Acad. Sci. USA (1982) 79, 5392–5395; Carelli et al., Int. J. Immunopharmacol. (1985) 7, 215–224). However, due to the apparent pyrogenic effects of MDP, this technique of immunological castration is also likely to prove unacceptable for general use in veterinary practice.

SUMMARY OF THE INVENTION

With the aim of overcoming the above-mentioned problems, we have now designed analogues of LHRH with a short peptide extension at the C-terminus of the native amino acid sequence, which we have predicted by potential energy calculations to have substantially the same conformation as native LHRH in solution and may be readily linked to a polypeptide carrier via the side chain of a cysteine or tyrosine residue provided at the C-terminus.

According to one aspect of the present invention, we thus provide an analogue of LHRH having the amino acid sequence
pGlg-His-Trp-Ser-Tyr-X-Leu-Arg-Pro-Gly-Y-Z wherein X represents Gly or a D-amino acid, Y represents one or more amino acid residues, which may be the same or different, and Z represents Cys or Tyr, such that the solution conformation of said analogue is substantially similar to that of native LHRH.

DESCRIPTION OF THE PREFERRED EMBODIMENTS

Figure 1:
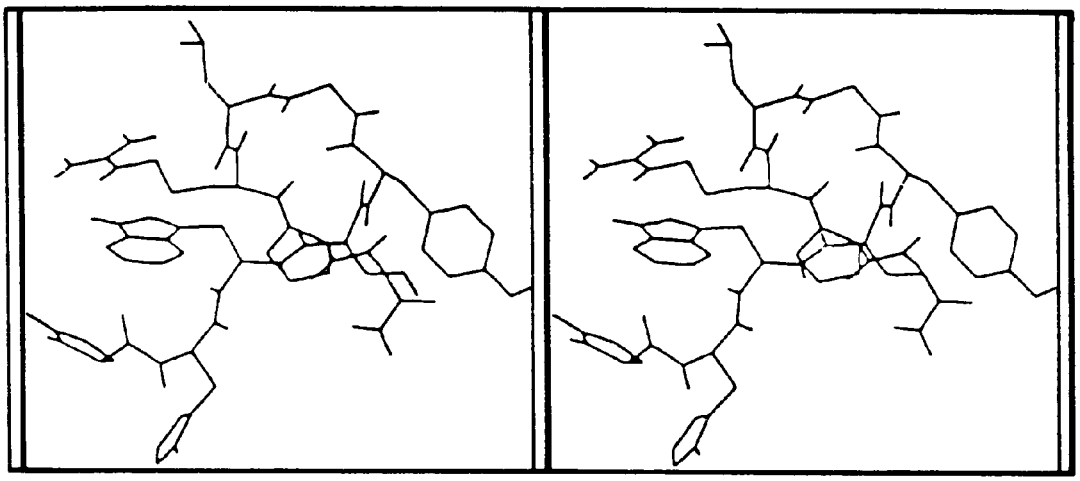
FIGS. 1(a) and 1(b) are stereoscopic diagrams of the predicted lowest energy solution conformers of mammalian LHRH and the LHRH-Gly-Cys-OH analogues according to the present invention, respectively.
Figure 1:
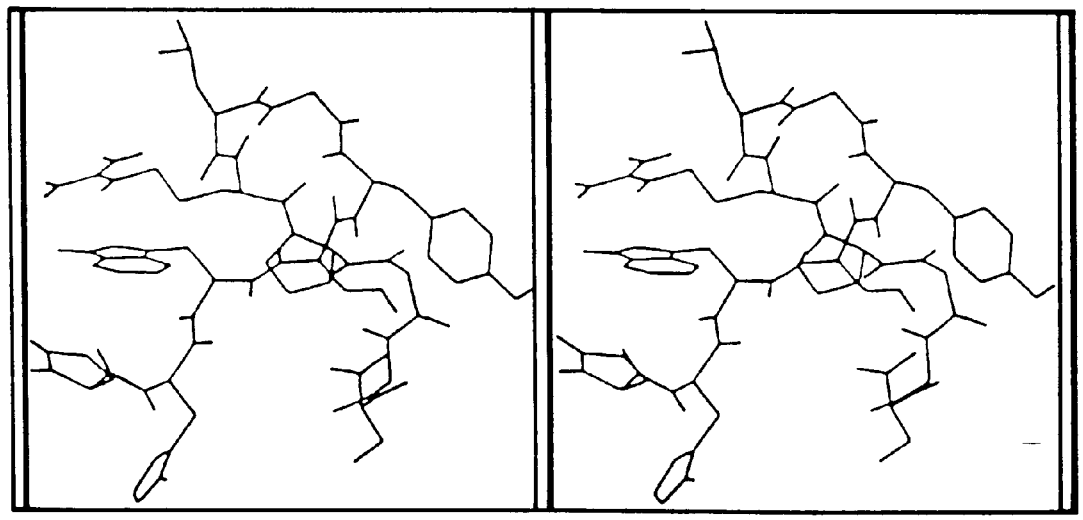

Preferably, the C-terminal extension consists of 1–3 glycine residues followed by a cysteine or tyrosine residue at the C-terminus, most preferably a single glycine residue followed by a cysteine residue (the analogue of this type wherein the native LHRH sequence is joined to a Gly-Cys extension will hereinafter be referred to as LHRH-Gly-Cys-OH). Computer-aided potential energy calculations have indicated that these preferred LHRH analogues preferably adopt a conformation in solution virtually identical to the type II' turn around Gly$^6$-Leu$^7$ predicted as the lowest energy solution conformation for native LHRH.

By substituting for the Gly residue at position 6 in an extended LHRH analogue as above a D-amino acid, e.g. D-Ala, D-Lys or D-Ser(tBu), further advantageous extended LHRH analogues may be obtained without radical alteration of the solution conformation. Such analogues may be expected to have the benefit of improved stability to degradation in vivo.

The novel analogues may be synthesised by standard peptide synthesis techniques, e.g. by the FMOC-polyamide method using the solid phase resin developed by Arshady, R. et al. (J. Chem. Soc. Perkin Trans. (1981) 1, 529–537) and fluorenyl-methoxycarbonyl (FMOC) protection of the individual amino acids incorporated (Atherton, E. et al., J. Chem. Soc. Perkin Trans. (1983) 1, 65–73).

The novel analogues may also be synthesised indirectly by DNA synthesis and conventional techniques of genetic engineering.

Another aspect of the present invention therefore provides DNA molecules coding for at least one extended LHRH analogue as described herein preferably incorporated into a suitable expression vector replicable in microorganisms or in mammalian cells.

According to a further aspect of the present invention, we provide an extended LHRH analogue as hereinbefore described conjugated to a polypeptide carrier e.g. via the side chain of the C-terminal cysteine or tyrosine residue. Formation of such an LHRH analogue-carrier conjugate may conveniently be achieved by modification of one or more lysine side chains of the carrier polypeptide with maleimide, e.g. by treatment with N-γ-maleimidobutyryloxysuccinimide (Calbiochem), and subsequent coupling of the LHRH analogue via the side chain of the C-terminal cysteine residue to give a thioether bond. Analogues having a terminal tyrosine residue may be coupled to a carrier polypeptide e.g. by a diazo bond formed with N-(4-diazophenyl) maleimide. Other coupling reactions and reagents may of course be used to equivalent effect. The conjugate may also, in principle, be produced via a DNA molecule coding therefor which is preferably incorporated into a suitable expression vector replicable in microorganisms or in mammalian cells.

We believe that in such conjugates the LHRH moiety substantially retains the free solution conformation which is optimal for production of anti-LHRH antibodies, since the linkage is both flexible and of sufficient length to hold the peptide away from the surface of the carrier.

By employing conjugates of LHRH analogues of this type, it has been found possible to achieve effective adjuvant-free immunisation to LHRH in mammals and we consider this technique to be a highly desirable alternative to surgical castration for veterinary control of reproductive function, e.g. in dogs, cats and horses. Moreover, in the case of humans having an androgen-sensitive or oestrogen-sensitive carcinoma, e.g. prostate carcinoma or mammary carcinoma, use of such conjugates to induce anti-LHRH antibody production and thus lower steroid levels may also be beneficial.

For immunisation of a wide range of mammals to LHRH, examples of preferred carriers include purified protein derivative of tuberculin (Central Veterinary Laboratory, Weybridge, U.K.) and tetanus toxoid (Wellcome), purified protein derivative of tuberculin being most favoured. When using purified protein derivative of tuberculin (commonly referred to as PPD) as the carrier for production of anti-LHRH antibodies, in order to achieve a high titre of the required antibodies it is desirable for the recipient of the LHRH analogue—PPD conjugate to be tuberculin sensitive, e.g. by virtue of an earlier BCG vaccination, as previously described for antibody production to other hapten-PPD conjugates (Lachmann et al. in "Synthetic Peptides as Antigens", Ciba Foundation Symposium 119 (1986) pp. 25–40). In the U.K. and many other countries, the population is offered BCG vaccination and is therfore largely PPD-sensitive. Hence, LHRH analogue-PPD conjugates of the present invention are considered highly advantageous for use in the clinical control of carcinoma in humans.

According to a still further aspect of the present invention, we provide a method of reducing fertility in a mammal which comprises immunising said mammal with an extended LHRH analogue or with a carrier conjugate thereof as hereinbefore described so as to produce a titre of anti-LHRH antibodies sufficient to significantly reduce the biological efficacy of endogenous LHRH. Normally no adjuvant is necessary. In a particularly preferred embodiment of this method, an LHRH analogue-PPD conjugate of the present invention is administered intradermally in isotonic saline, if necessary after priming of the recipient with BCG vaccine to achieve tuberculin sensitivity. For such an immunisation protocol, it is particularly desirable to employ the thioether conjugate of maleimide—modified PPD and LHRH-Gly-Cys-OH (hereinafter referred to as LHRH-Gly-Cys-OH-PPD).

The following non-limiting example further illustrates the present invention.

EXAMPLE

1. Solution conformation analysis of LHRH-Gly-Cys-OH

The conformational preferences in solution of LHRH and LHRH-Gly-Cys-OH (see FIGS. 1(a) and 1(b)) were studied using the LUCIFER program for potential energy minimisation (Robson and Platt, J. Mol. Biol. (1986) 188, 259–281). The program was run on a CDC Cyber 205 computer and solvent effects were modelled using the representation previously used for a study of neurotensin (Ward et al., Regul. Peptides (1986) 15, 197)

From energy-minimisation studies, we have discovered that LHRH-Gly-Gly-Cys-OH and LHRH-Gly-Gly-Gly-Cys-OH also have very similar solution conformations to LHRH.

2. Preparation of LHRH-Gly-Cys-OH-PPD and other LHRH analogue-carrier conjugates.

Bovine PPD (10 mg, Batch no. 291, Central Veterinary Laboratory, Weybridge, U.K.) was dissolved in 0.5 ml of 0.05M NAKPO$_4$, 0.14M NaCl, pH 7.0 (buffer A) and treated with 1 mg N-γ-maleimidobutyryloxysuccinimide (Calbiochem) previou sly dissolved in 5 ul freshly distilled, dry dimethyl formamide. The mixture was stirred for 1 hour at 23° C. and applied to a column of Sephadex G25 (0.9×25 cm) equilibrated with buffer A. The modified PPD eluting in the excluded volume was transferred to a stoppered vessel and to it was added dropwise, with stirring, 10 mg of LHRH-Gly-Cys-OH (85% purity ) dissolved in 1 ml of buffer A previously degassed and purged with nitrogen. The mixture was stirred at 23° C. under nitrogen for 2 hours and the amount of LHRH which bound to the PPD determined by estimating the free thiol content of the mixture at regular intervals using 5,5'-dithiobis(2-nitrobenzoic acid) (Sigma) according to the method of Deakin et al. (Biochem. J. (1963) 89, 296–304). A coupling efficiency of 65% was noted. The conjugate was extensively dialysed against several changes of distilled water at 4° C., lyophilised, and stored at −20° C. before use.

Tetanus toxoid (TT) (Wellcome) and bovine serum albumin (BSA) (Sigma) were conjugated to LHRH-Gly-Cys-OH exactly as described for PPD above.

3. Immunisation studies with rats (a) Immunisation schedule

Groups of 5 male rats (AO×DA, $F_1$ rats, 4 months old) were immunised with an amount of conjugate equivalent to 50 ug LHRH-Gly-Cys-OH according to the following schedule. Groups 1 and 2 received LHRH-Gly-Cys-OH-PPD intradermally in saline. Groups 3 and 4 received LHRH-Gly-Cys-OH-PPD as an alum precipitate subcutaneously. Groups 5 and 6 received LHRH-Gly-Cys-OH-TT subcutaneously in alum or Freund's complete adjuvant (FCA) respectively. Group 7 received no immunisation. Groups 1 and 3 received BCG vaccine (Glaxo) equivalent to one half the human dose one month prior to the first immunisation with conjugate. Immunisation consisted of a primary injection followed by two booster injections at one monthly intervals.

The animals in the study were subsequently bled by cannulation of the tail artery at fortnightly intervals for estimation of antibody titres, and then were sacrificed 3 months after the primary immunisation, the testes removed, weighed and subjected to histological examination.

Estimation of anti-LHRH antibody titre was achieved by ELISA using plastic microtitre plates coated with LHRH-Gly-Cys-OH-BSA. Assays were developed with 1:1000 dilution of goat anti-rat 1 gG alkaline phosphatase conjugate.

Removed testes were fixed in neutral buffered formalin, embedded in paraffin wax and 5 micron sections cut. Sections were stained with haematoxylin and eosin.

(b) Results (i) Antibody titres to LHRH

Figure 2:
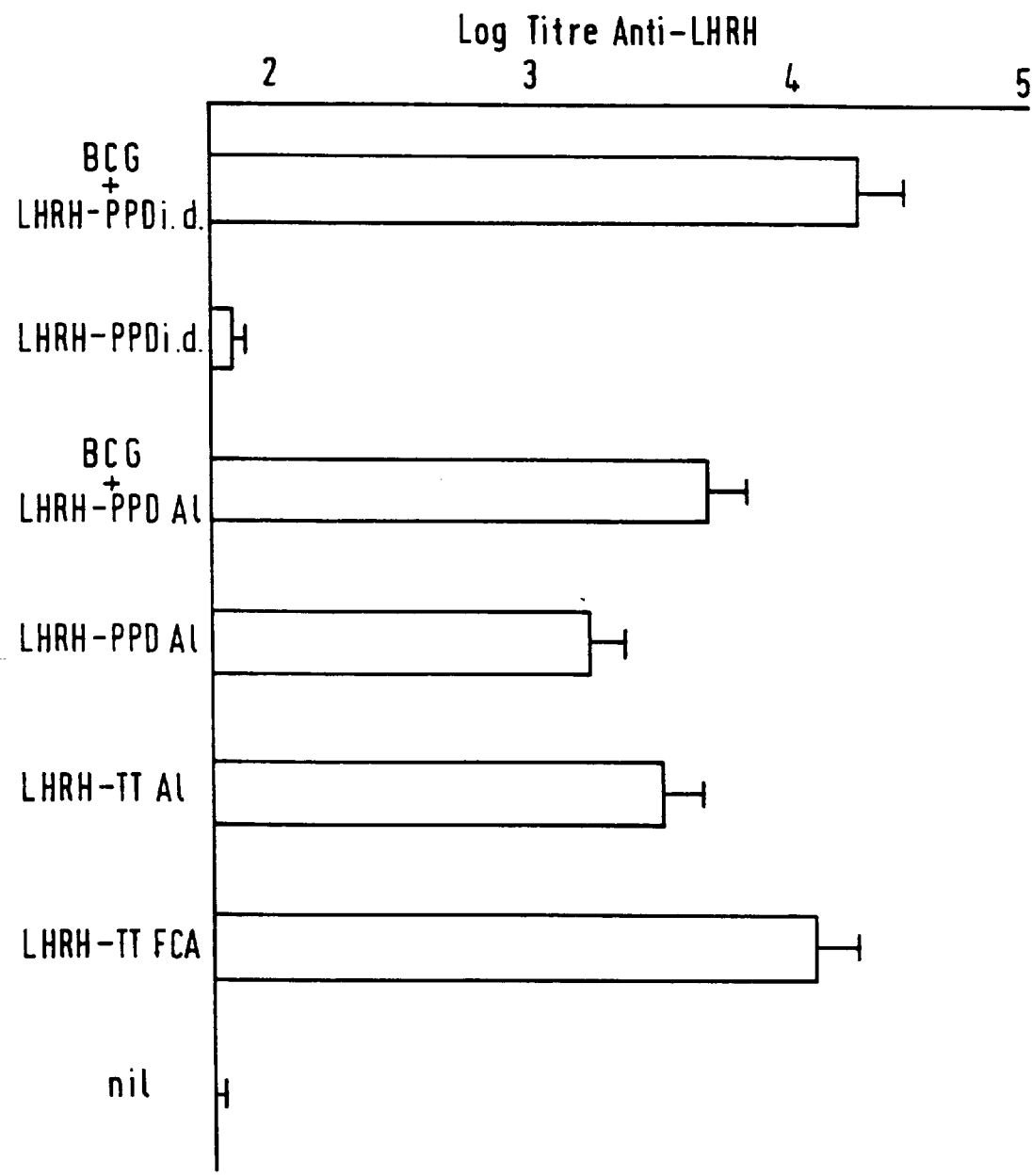
FIG. 2 is a bar chart of Day 70 anti-LHRH-Gly-Cys-OH antibody titres in rats immunized with various LHRH-Gly-Cys-OH conjugates.

Each of the groups of rats immunised with LHRH-Gly-Cys-OH conjugates gave an antibody response to the hormone detectable by ELISA. FIG. 2 shows the antibody titres at week 10 for each group. Immunisation with the conjugate of LHRH-Gly-Cys-OH-TT led to significant antibody levels, and these were higher in the group receiving conjugate in FCA. Although all four groups of rats receiving LHRH-Gly-Cys-OH-PPD gave antibody responses, the responses in those groups (1 and 3) previously primed with BCG, were considerably higher than in those which were not (2 and 4). LHRH-Gly-Cys-OH-PPD given intrademally was a very poor immunogen in normal rats, but in the BCG primed animals led to the highest titre of antibody seen in any of the groups. LHRH-Gly-Cys-OH-PPD absorbed onto alum and given subcutaneously led to significant antibody production in normal rats, but in the BCG primed rats the response was inferior to that obtained with the soluble antigen given intradermally.

(ii) Physiological effects of immunisation to LHRH

Figure 3:
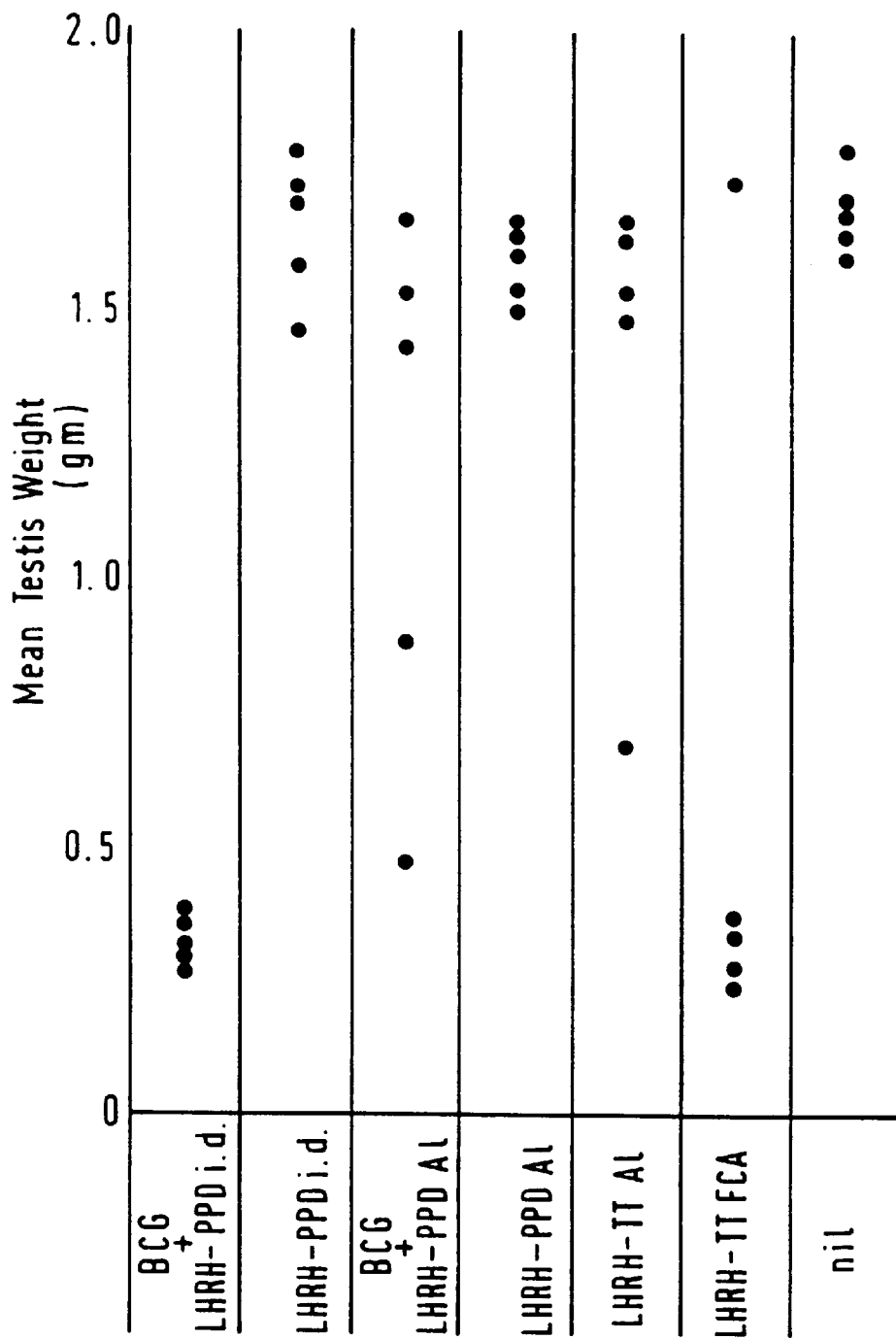
FIG. 3 is a plot of the effect of immunization with various LHRH-Gly-Cys-OH conjugates on testicular weight in rats.

Mean testis weights for individual rats in each group are shown in FIG. 3. Marked testicular regression was apparent in all members of the group receiving soluble LHRH-Gly-Cys-OH-PPD after BCG priming and also in the group treated with LHRH-Gly-Cys-OH-TT in FCA athough, here, one animal showed no effects. Less marked effects were seen in Group 3 (2 of 5) and Group 5 (1 of 5). Histological examination of testes revealed that in those individuals exhibiting severe regression there was evidence of marked atrophy of seminiferous tubules and absence of spermatogenesis.

In further studies, a conjugate of LHRH and PPD prepared using a water soluble carbodiimide in conventional manner was shown to be unable to induce a physiological response when used to immunise rats subcutaneously or intradermally in the absence of an adjuvant. D-Lys$^6$-LHRH conjugated to PPD with glutaraldehyde was likewise found to be ineffective.

We claim:

1. An analogue of luteinizing hormone-releasing hormone (LHRH) comprising the amino acid sequence:

pGlg-His-Trp-Ser-Tyr-X-Leu-Arg-Pro-Gly-Y-Z wherein X represent Gly or a D-amino acid, Y represents more than one amino acid residue, which may be the same or different, and Z is selected from the group consisting of Cys or Tyr, such that the solution conformation of the LHRH moiety of said analogue is substantially similar to that of native LHRH.

2. The analogue of claim 1, wherein X represents Gly.

3. The analogue of claim 1, wherein X is selected from D-Ala, D-Lys or D-Ser(tBu).

4. The analogue of claim 1 wherein Y is 2 or 3 glycine residues.

5. A vaccine comprising the LHRH analogue of claim 1, or to a polypeptide vaccine carrier, together with a pharmaceutically acceptable excipient.

6. A method of reducing fertility in a mammal which comprises immunising said mammal with the LHRH analogue of claim 1, so as to produce a titre of anti-LHRH antibodies sufficient to reduce significantly the biological efficacy of endogenous LHRH.

7. A method for the clinical control of androgen-sensitive or oestrogen-sensitive carcinoma which comprises administering to the patient an effective amount of the LHRH analogue of claim 1, so as to significantly reduce androgen or oestrogen levels in said patient.

8. An adjuvant-free vaccine consisting essentially of an LHRH analogue according to claim 1, or a C-terminal conjugate of said analogue to a polypeptide vaccine carrier, together with a pharmaceutically acceptable excipient.

9. An analogue of luteinising hormone-releasing hormone (LHRH) having the amino acid sequence:

wherein X represents Gly or a D-amino acid, Y represents a single amino acid residue other than Gly and Z is selected from the group consisting of Cys and Tyr, such that the solution conformation of said analogue is substantially similar to that of native LHRH.

10. A method of reducing fertility in a mammal which comprises immunizing said mammal with the LHRH analogue of claim 9, such that biological efficacy of endogenous LHRH in said mammal is reduced.

11. A method for the clinical control of androgen-sensitive or oestrogen-sensitive carcinoma comprising the step of administering to a patient an effective amount of the LHRH analogue of claim 9, so as to significantly reduce androgen or oestrogen levels in said patient.

12. A method of making an LHRH analogue as claimed in claim 1, wherein said analogue is synthesized directly by peptide synthesis, indirectly by DNA synthesis or is obtained from a microorganism or mammalian cell engineered to express said analogue.

13. A method of making an LHRH analogue as claimed in claim 9, wherein said analogue is synthesized directly by peptide synthesis, indirectly by DNA synthesis or is obtained from a microorganism or mammalian cell engineered to express said analogue.

* * * * *